(12) United States Patent
Zhu (10) Patent No.: US 10,375,992 B2
(45) Date of Patent: Aug. 13, 2019

(54) TAMPER-PROOF LOCKING MECHANISMS AND ELECTRONIC CIGARETTES HAVING THE SAME

(71) Applicant: Xiaochun Zhu, Shenzhen (CN)

(72) Inventor: Xiaochun Zhu, Shenzhen (CN)

(73) Assignee: SHENZHEN KANGER TECHNOLOGY CO., LTD, Shenzhen (CN)

( * ) Notice: Subject to any disclaimer, the term of this patent is extended or adjusted under 35 U.S.C. 154(b) by 0 days.

(21) Appl. No.: 15/023,665

(22) PCT Filed: Mar. 16, 2016

(86) PCT No.: PCT/CN2016/076542
§ 371 (c)(1),
(2) Date: Mar. 21, 2016

(87) PCT Pub. No.: WO2017/156733
PCT Pub. Date: Sep. 21, 2017

(65) Prior Publication Data
US 2018/0368471 A1    Dec. 27, 2018

(51) Int. Cl.
*A24F 47/00*     (2006.01)
*A61M 15/06*    (2006.01)
*A24F 7/02*      (2006.01)

(52) U.S. Cl.
CPC ............. *A24F 47/008* (2013.01); *A24F 7/02* (2013.01); *A61M 15/06* (2013.01)

(58) Field of Classification Search
CPC ........... A24F 47/00–008; A61M 15/06; A61M 15/009; A61M 15/0091; A61M 2202/0468
See application file for complete search history.

(56) References Cited

U.S. PATENT DOCUMENTS

| 9,010,335 B1* | 4/2015 | Scatterday | A24F 47/008 128/202.21 |
| 2015/0027467 A1* | 1/2015 | Liu | A24F 47/008 131/329 |
| 2018/0255836 A1* | 9/2018 | Qiu | A24F 47/008 |

FOREIGN PATENT DOCUMENTS

| CN | 105380299 | * 3/2016 | A24F 47/008 |
| WO | WO-2015172331 A1 | * 11/2015 | A24F 47/00 |

OTHER PUBLICATIONS

WO-2015172331-A1 (Machine Translation) [online], [retrieved on May 16, 2019], retrieved from Google Patents (https://patents.google.com/) (Year: 2015).*

(Continued)

*Primary Examiner* — Michael H. Wilson
*Assistant Examiner* — Yana B Krinker
(74) *Attorney, Agent, or Firm* — Ming Jiang; MM IP Services LLC (57) ABSTRACT

Certain aspects of present invention relate to an electronic cigarette having temper-proof locking mechanisms. In certain embodiments, the electronic cigarette may include: an electronic cigarette body, a temper-proof mouthpiece connector locking mechanism threadedly connected to electronic cigarette body, and a temper-proof power connector locking mechanism threadedly connected to electronic cigarette body. When a user pushes temper-proof mouthpiece connector locking mechanism towards electronic cigarette body, temper-proof mouthpiece connector locking mechanism is locked such that the user is able to remove a mouthpiece connector from electronic cigarette body to refill e-liquid for the electronic cigarette. When user pushes temper-proof power connector locking mechanism towards electronic cigarette body, temper-proof power connector locking mechanism is locked such that user is able to remove a power connector from electronic cigarette body to replace (Continued)

a vaporizer, a heater for the vaporizer, and e-liquid storage medium of the electronic cigarette.

8 Claims, 6 Drawing Sheets

(56) References Cited

OTHER PUBLICATIONS

CN 105380299 (Machine Translation) [online], [retrieved on May 16, 2019], retrieved from Google Patents (https://patents.google.com/) (Year: 2016).*

* cited by examiner

TAMPER-PROOF LOCKING MECHANISMS AND ELECTRONIC CIGARETTES HAVING THE SAME

FIELD

The present invention generally relates to the field of electronic cigarettes, and more particularly to electronic cigarettes having temper-proof locking mechanisms.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

It is well known that smoking cigarette is harmful to smoker's health. The active ingredient in a cigarette is mainly nicotine. During smoking, nicotine, along with tar aerosol droplets produced in the cigarette burning, are breathed into the alveolus and absorbed quickly by the smoker. Once nicotine is absorbed into the blood of the smoker, nicotine then produces its effect on the receptors of the smoker's central nervous system, causing the smoker relax and enjoy an inebriety similar to that produced by an exhilarant.

The electronic cigarette is sometimes referred as electronic vaporing device, personal vaporizer (PV), or electronic nicotine delivery system (ENDS). It is a battery-powered device which simulates tobacco smoking. It generally uses a heating element that vaporizes a liquid solution (e-liquid). Some solutions contain a mixture of nicotine and a variety of flavorings, while others release a flavored vapor without nicotine. Many are designed to simulate smoking experience, such as cigarette smoking or cigar smoking. Some of them are made with similar appearance, while others are made considerably different in appearance.

Conventional electronic cigarettes are made with a mouthpiece assembly, a vaporizer assembly, an electric connecting assembly, and an e-liquid storage assembly. The mouthpiece is installed on top of the e-liquid storage assembly, and the vaporizer assembly is installed inside of the e-liquid storage assembly, and electrically connected to a DC power source through the electric connecting assembly. The mouthpiece assembly is connected to the vaporizer assembly and forms an air flow passage. The e-liquid is stored in the e-liquid storage assembly. The e-liquid flows through a vaporizing chamber of the heating assembly using fiber threads. The e-liquid in the fiber threads is then heated by a heating wire of the heating assembly and therefore vaporized. The vaporized e-liquid goes up to the mouthpiece such that a smoker enjoys the vaporized e-liquid.

Regular maintenance of electronic cigarettes may include refilling e-liquid, and occasionally replacing the vaporizers, heaters for the vaporizers, and e-liquid storage media. Certain electronic cigarettes may include mechanisms so that such maintenance may be performed. For example, certain electronic cigarettes have a mouthpiece assembly for refilling the e-liquid, and a power connector assembly for replacing the vaporizers, heaters for the vaporizers, and e-liquid storage media. However, sometimes, unauthorized disassembling the mouthpiece assembly, and/or the power connector assembly may happen, especially for families having children. Therefore, it is desirable to have certain temper-proof mechanisms so that such unauthorized access and tempering are prevented.

Therefore, an unaddressed need exists in the art to address the aforementioned deficiencies and inadequacies.

SUMMARY

In one aspect, the present invention relates to a temper-proof mouthpiece connector locking mechanism for an electronic cigarette. In certain embodiments, the temper-proof mouthpiece connector locking mechanism may include: a mouthpiece connector base, a mouthpiece connector, a mouthpiece connector temper-proof ring, one or more mouthpiece connector locking pins, and one or more mouthpiece connector locking springs. The mouthpiece connector base may include a mouthpiece connector outside thread configured to threadedly connect to a mouthpiece connector inside thread of an electronic cigarette body. The mouthpiece connector base defines one or more mouthpiece connector locking openings. The mouthpiece connector may be fixedly connected to the mouthpiece connector base. The mouthpiece connector temper-proof ring may be positioned outside of the mouthpiece connector for preventing mouthpiece connector tempering. The temper-proof mouthpiece connector locking mechanism may include an equal number of mouthpiece connector locking pins as the one or more mouthpiece connector locking openings.

In certain embodiments, when a user pushes the mouthpiece connector temper-proof ring towards the mouthpiece connector base against a resilient force of the one or more mouthpiece connector locking springs, each of the one or more mouthpiece connector locking pins engages a corresponding one of the one or more mouthpiece connector locking openings such that the user can remove the mouthpiece connector from the electronic cigarette body by turning the temper-proof mouthpiece connector locking mechanism.

In certain embodiments, when the user releases the mouthpiece connector temper-proof ring, each of the one or more mouthpiece connector locking pins disengages the corresponding one of the one or more mouthpiece connector locking openings at the resilient force of the one or more mouthpiece connector locking springs such that the user will not be able to remove the mouthpiece connector from the electronic cigarette body.

In certain embodiments, when the mouthpiece connector is removed from the electronic cigarette body, the user may refuel e-liquid to an e-liquid storage tank of the electronic cigarette.

In another aspect, the present invention relates to a temper-proof power connector locking mechanism for an electronic cigarette. In certain embodiments, the temper-proof power connector locking mechanism may include: a power connector base, a power connector, a power connector temper-proof ring, one or more power connector locking pins, and one or more power connector locking springs. The power connector base may include a power connector outside thread configured to threadedly connect to a power connector inside thread of an electronic cigarette body. The power connector base defines one or more power connector locking openings. The power connector may be fixedly connected to the power connector base. The power connector temper-proof ring may be positioned outside of the power connector for preventing power connector tempering. The temper-proof power connector locking mechanism may include an equal number of power connector locking pins as the one or more power connector locking openings.

In certain embodiments, when a user pushes the power connector temper-proof ring towards the power connector base against a resilient force of the one or more power connector locking springs, each of the one or more power connector locking pins engages a corresponding one of the one or more power connector locking openings such that the user can remove the power connector from the electronic cigarette body by turning the temper-proof power connector locking mechanism.

In certain embodiments, when the user releases the power connector temper-proof ring, each of the one or more power connector locking pins disengages the corresponding one of the one or more power connector locking openings at the resilient force of the one or more power connector locking springs such that the user will not be able to remove the power connector from the electronic cigarette body.

In certain embodiments, when the power connector is removed from the electronic cigarette body, the user may replace a vaporizer of the electronic cigarette, a heater for the vaporizer, and an e-liquid storage medium.

In yet another aspect, the present invention relates to an electronic cigarette having a temper-proof locking mechanisms. In certain embodiments, the electronic cigarette may include: an electronic cigarette body having a mouthpiece connector inside thread and a power connector inside thread, a temper-proof mouthpiece connector locking mechanism threadedly connected to the mouthpiece connector inside thread of the electronic cigarette body, and a temper-proof power connector locking mechanism threadedly connected to the power connector inside thread of the electronic cigarette body.

In certain embodiments, when a user pushes the temper-proof mouthpiece connector locking mechanism towards the electronic cigarette body, the temper-proof mouthpiece connector locking mechanism is locked such that the user is able to remove a mouthpiece connector from the electronic cigarette body to refill e-liquid for the electronic cigarette. When the user pushes the temper-proof power connector locking mechanism towards the electronic cigarette body, the temper-proof power connector locking mechanism is locked such that the user is able to remove a power connector from the electronic cigarette body to replace a vaporizer, a heater for the vaporizer, and e-liquid storage medium of the electronic cigarette.

In certain embodiments, the temper-proof mouthpiece connector locking mechanism may include: a mouthpiece connector base, a mouthpiece connector, a mouthpiece connector temper-proof ring, one or more mouthpiece connector locking pins, and one or more mouthpiece connector locking springs. The mouthpiece connector base may include a mouthpiece connector outside thread configured to threadedly connect to the mouthpiece connector inside thread of the electronic cigarette body. The mouthpiece connector base defines one or more mouthpiece connector locking openings. The mouthpiece connector may be fixedly connected to the mouthpiece connector base. The mouthpiece connector temper-proof ring may be positioned outside of the mouthpiece connector for preventing mouthpiece connector tempering. The temper-proof mouthpiece connector locking mechanism may include an equal number of mouthpiece connector locking pins as the one or more mouthpiece connector locking openings.

In certain embodiments, when a user pushes the mouthpiece connector temper-proof ring towards the mouthpiece connector base against a resilient force of the one or more mouthpiece connector locking springs, each of the one or more mouthpiece connector locking pins engages a corresponding one of the one or more mouthpiece connector locking openings such that the user can remove the mouthpiece connector from the electronic cigarette body by turning the temper-proof mouthpiece connector locking mechanism, and when the user releases the mouthpiece connector temper-proof ring, each of the one or more mouthpiece connector locking pins disengages the corresponding one of the one or more mouthpiece connector locking openings at the resilient force of the one or more mouthpiece connector locking springs such that the user will not be able to remove the mouthpiece connector from the electronic cigarette body.

In certain embodiments, the temper-proof power connector locking mechanism may include: a power connector base, a power connector, a power connector temper-proof ring, one or more power connector locking pins, and one or more power connector locking springs. The power connector base may include a power connector outside thread configured to threadedly connect to the power connector inside thread of the electronic cigarette body. The power connector base defines one or more power connector locking openings. The power connector may be fixedly connected to the power connector base. The power connector temper-proof ring may be positioned outside of the power connector for preventing power connector tempering. The temper-proof power connector locking mechanism may include an equal number of power connector locking pins as the one or more power connector locking openings.

In certain embodiments, when a user pushes the power connector temper-proof ring towards the power connector base against a resilient force of the one or more power connector locking springs, each of the one or more power connector locking pins engages a corresponding one of the one or more power connector locking openings such that the user can remove the power connector from the electronic cigarette body by turning the temper-proof power connector locking mechanism. When the user releases the power connector temper-proof ring, each of the one or more power connector locking pins disengages the corresponding one of the one or more power connector locking openings at the resilient force of the one or more power connector locking springs such that the user will not be able to remove the power connector from the electronic cigarette body.

In certain embodiments, when the power connector is removed from the electronic cigarette body, the user may replace a vaporizer of the electronic cigarette, a heater for the vaporizer, and an e-liquid storage medium.

In certain embodiments, the electronic cigarette may also include: a mouthpiece connected to the mouthpiece connector, and a power source connected to the power connector. The power source may include a positive terminal and a negative terminal, and an insulation layer between the positive terminal, and the negative terminal.

These and other aspects of the present invention will become apparent from the following description of the preferred embodiment taken in conjunction with the following drawings, although variations and modifications therein may be effected without departing from the spirit and scope of the novel concepts of the invention.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment. The drawings do not limit the present invention to the specific embodiments disclosed and described herein. The drawings are not necessarily to scale, emphasis instead being placed upon clearly illustrating the principles of the invention, and wherein.

DETAILED DESCRIPTION

The present invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom", "upper" or "top," and "front" or "back" may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximates, meaning that the term "around", "about" or "approximately" can be inferred if not expressly stated.

Many specific details are provided in the following descriptions to make the present invention be fully understood, but the present invention may also be implemented by using other manners different from those described herein, so that the present invention is not limited by the specific embodiments disclosed in the following.

The description will be made as to the embodiments of the present invention in conjunction with the accompanying drawings FIGS. 1 through 7. In accordance with the purposes of this invention, as embodied and broadly described herein, this invention, in one aspect, the present invention relates to a temper-proof mouthpiece connector locking mechanism 10 for an electronic cigarette.

Figure 1A:
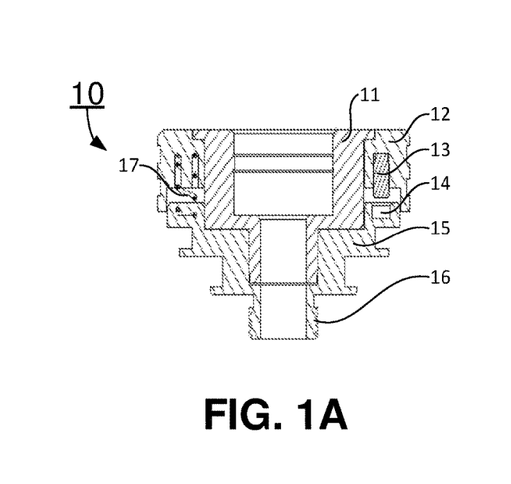
FIG. 1A is a cross-sectional view of a temper-proof mouthpiece connector locking mechanism in an unlocked position.
Figure 1B:
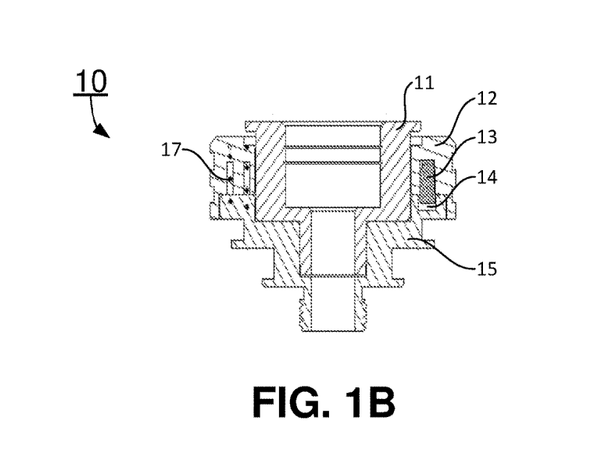
FIG. 1B is a cross-sectional view of the temper-proof mouthpiece connector locking mechanism in a locked position according to certain embodiments of the present invention.

Referring now to FIG. 1A and FIG. 1B, a cross-sectional view of a temper-proof mouthpiece connector locking mechanism in an unlocked position, and a cross-sectional view of the temper-proof mouthpiece connector locking mechanism in a locked position are shown according to certain embodiments of the present invention.

In certain embodiments, the temper-proof mouthpiece connector locking mechanism 10 may include: a mouthpiece connector base 15, a mouthpiece connector 11, a mouthpiece connector temper-proof ring 12, one or more mouthpiece connector locking pins 13, and one or more mouthpiece connector locking springs 17. The mouthpiece connector base 15 may include a mouthpiece connector outside thread 16 configured to threadedly connect to a mouthpiece connector inside thread 31 of an electronic cigarette body 30. The mouthpiece connector base 15 defines one or more mouthpiece connector locking openings 14. The mouthpiece connector 11 may be fixedly connected to the mouthpiece connector base 15. The mouthpiece connector temper-proof ring 12 may be positioned outside of the mouthpiece connector 11 for preventing mouthpiece connector tempering. The temper-proof mouthpiece connector locking mechanism 10 may include an equal number of mouthpiece connector locking pins 13 as the one or more mouthpiece connector locking openings 14.

In certain embodiments, when a user pushes the mouthpiece connector temper-proof ring 12 towards the mouthpiece connector base 15 against a resilient force of the one or more mouthpiece connector locking springs 17 as shown in FIG. 1B, each of the one or more mouthpiece connector locking pins 13 engages a corresponding one of the one or more mouthpiece connector locking openings 14 such that the user can remove the mouthpiece connector 11 from the electronic cigarette body 30 by turning the temper-proof mouthpiece connector locking mechanism 10.

In certain embodiments, when the user releases the mouthpiece connector temper-proof ring 12 as shown in FIG. 1A, each of the one or more mouthpiece connector locking pins 13 disengages the corresponding one of the one or more mouthpiece connector locking openings 14 at the resilient force of the one or more mouthpiece connector locking springs 17 such that the user will not be able to remove the mouthpiece connector 11 from the electronic cigarette body 30.

In certain embodiments, when the mouthpiece connector 11 is removed from the electronic cigarette body 30, the user may refuel e-liquid to an e-liquid storage tank of the electronic cigarette.

In certain embodiments, the one or more mouthpiece connector locking pins 13 are substantially evenly distributed along a top surface of the mouthpiece connector base 15, and the corresponding one or more mouthpiece connector locking openings 14 are substantially evenly distributed along an inside edge of the mouthpiece connector 11, respectively, such that each of the one or more mouthpiece connector locking pins 13 engages a corresponding one of the one or more mouthpiece connector locking openings 14 when the user pushes the mouthpiece connector temper-proof ring 12 towards the mouthpiece connector base 15.

In one embodiment, the temper-proof mouthpiece connector locking mechanism 10 may include three mouthpiece connector locking springs 17 substantially evenly distributed along the top surface of the mouthpiece connector base 15. In certain embodiments, in order to move the mouthpiece connector temper-proof ring 12 up and down evenly, at least three mouthpiece connector locking springs 17 may be needed. In other embodiments, the temper-proof mouthpiece connector locking mechanism 10 may include more than three mouthpiece connector locking springs 17, evenly distributed along the top surface of the mouthpiece connector base 15.

In one embodiment, the temper-proof mouthpiece connector locking mechanism 10 may include one mouthpiece connector locking pin 13 and one corresponding mouthpiece connector locking opening 14. In another embodiment, the temper-proof mouthpiece connector locking mechanism 10 may include three mouthpiece connector locking pins 13 and three corresponding mouthpiece connector locking openings 14, respectively.

In certain embodiments, each of the one or more mouthpiece connector locking pins 13 may include: a round shape, a square shape, a triangular shape, a rectangular shape, an oval shape, and a combination of these shapes.

In another aspect, the present invention relates to a temper-proof power connector locking mechanism 20 for an electronic cigarette.

Figure 2A:
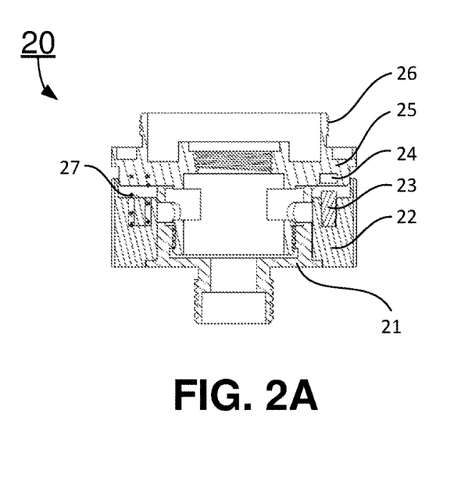
FIG. 2A is a cross-sectional view of a temper-proof power connector locking mechanism in an unlocked position.
Figure 2B:
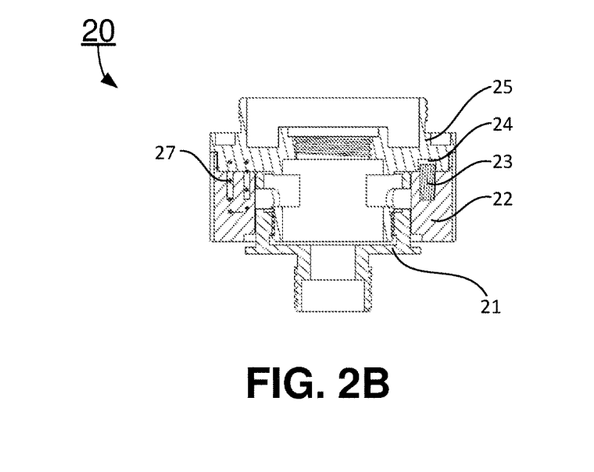
FIG. 2B is a cross-sectional view of the temper-proof power connector locking mechanism in a locked position according to certain embodiments of the present invention.

Referring now to FIG. 2A and FIG. 2B, a cross-sectional view of a temper-proof power connector locking mechanism 20 in an unlocked position, and a cross-sectional view of the temper-proof power connector locking mechanism 20 in a locked position are shown according to certain embodiments of the present invention.

In certain embodiments, the temper-proof power connector locking mechanism 20 may include: a power connector base 25, a power connector 21, a power connector temper-proof ring 22, one or more power connector locking pins 23, and one or more power connector locking springs 27. The power connector base 25 may include a power connector outside thread 26 configured to threadedly connect to a power connector inside thread 32 of an electronic cigarette body 30. The power connector base 25 defines one or more power connector locking openings 24. The power connector 21 may be fixedly connected to the power connector base 25. The power connector temper-proof ring 22 may be positioned outside of the power connector 21 for preventing power connector tempering. The temper-proof power connector locking mechanism 20 may include an equal number of power connector locking pins 23 as the one or more power connector locking openings 24.

In certain embodiments, when a user pushes the power connector temper-proof ring 22 towards the power connector base 25 against a resilient force of the one or more power connector locking springs 27, each of the one or more power connector locking pins 23 engages a corresponding one of the one or more power connector locking openings 24 such that the user can remove the power connector 21 from the electronic cigarette body 30 by turning the temper-proof power connector locking mechanism 20.

In certain embodiments, when the user releases the power connector temper-proof ring 22, each of the one or more power connector locking pins 23 disengages the corresponding one of the one or more power connector locking openings 24 at the resilient force of the one or more power connector locking springs 27 such that the user will not be able to remove the power connector 21 from the electronic cigarette body 30.

In certain embodiments, when the power connector 21 is removed from the electronic cigarette body 30, the user may replace a vaporizer of the electronic cigarette, a heater for the vaporizer, and an e-liquid storage medium.

In certain embodiments, the one or more power connector locking pins 23 are substantially evenly distributed along a bottom surface of the power connector temper-proof ring 22, and the corresponding one or more power connector locking openings 24 are substantially evenly distributed along a top surface of the power connector base 25, respectively, such that each of the one or more power connector locking pins 23 engages a corresponding one of the one or more power connector locking openings 24 when the user pushes the power connector temper-proof ring 22 towards the power connector base 25.

In certain embodiments, the temper-proof power connector locking mechanism 20 may include three power connector locking springs 27 substantially evenly distributed along the bottom surface of the power connector temper-proof ring 22. In certain embodiments, in order to move the power connector temper-proof ring 22 up and down evenly, at least three power connector locking springs 27 may be needed. In other embodiments, the temper-proof power connector locking mechanism 20 may include more than three power connector locking springs 27, substantially evenly distributed along the bottom surface of the power connector temper-proof ring 22.

In certain embodiments, each of the one or more power connector locking pins 23 may include: a round shape, a square shape, a triangular shape, a rectangular shape, an oval shape, and a combination of these shapes.

Figure 3A:
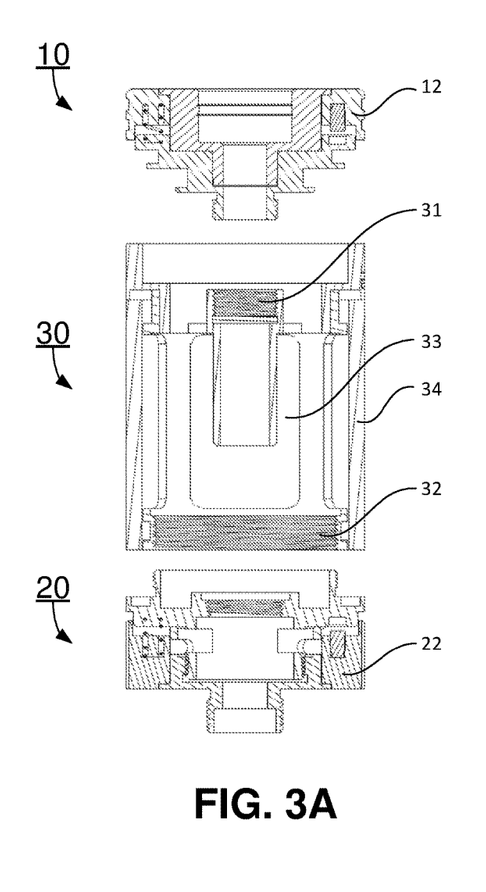
FIG. 3A is an exploded cross-sectional view of a part of an electronic cigarette having temper-proof locking mechanisms.

FIG. 3A shows an exploded cross-sectional view of a part of an electronic cigarette having temper-proof locking mechanisms in an unlocked position according to certain embodiments of the present invention. The electronic cigarette may include an electronic cigarette body 30. The electronic cigarette body 30 may include a mouthpiece connector inside thread 31, a power connector inside thread 32, a vaporizer 33, and an exterior wall 34 of an e-liquid storage tank.

In certain embodiments, the mouthpiece connector inside thread 31 is configured to threadedly connect to the mouthpiece connector outside thread 16 of the temper-proof mouthpiece connector locking mechanism 10. When the temper-proof mouthpiece connector locking mechanism 10 is disconnected or removed from the mouthpiece connector inside thread 31 of the electronic cigarette body 30. The user may refill e-liquid into the e-liquid storage tank.

In certain embodiments, the power connector inside thread 32 is configured to threadedly connect to the power connector outside thread 26 of the temper-proof power connector locking mechanism 20. When the temper-proof power connector locking mechanism 20 is disconnected or removed from the power connector inside thread 32 of the electronic cigarette body 30. The user may replace a vaporizer, a heater for the vaporizer, and e-liquid storage medium of the electronic cigarette 100.

Figure 3B:
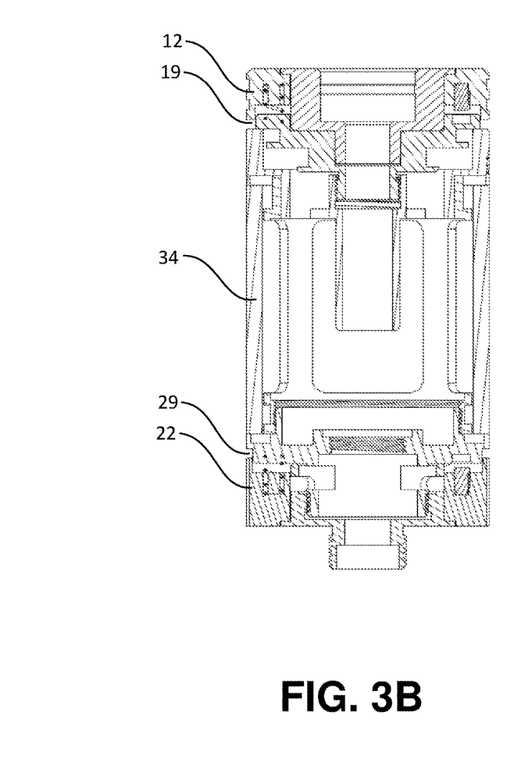
FIG. 3B is a cross-sectional view of the electronic cigarette having temper-proof locking mechanisms, both in an unlocked position according to certain embodiments of the present invention.

FIG. 3B shows a cross-sectional view of the assembled electronic cigarette having temper-proof locking mechanisms in an unlocked position according to certain embodiments of the present invention. When the temper-proof mouthpiece connector locking mechanism 10 is in an unlocked position, a first gap 19 may appear between the mouthpiece connector temper-proof ring 12 and the electronic cigarette body 30. When the temper-proof power connector locking mechanism 20 is in an unlocked position, a second gap 29 may appear between the power connector temper-proof ring 22 and the electronic cigarette body 30.

Figure 4A:
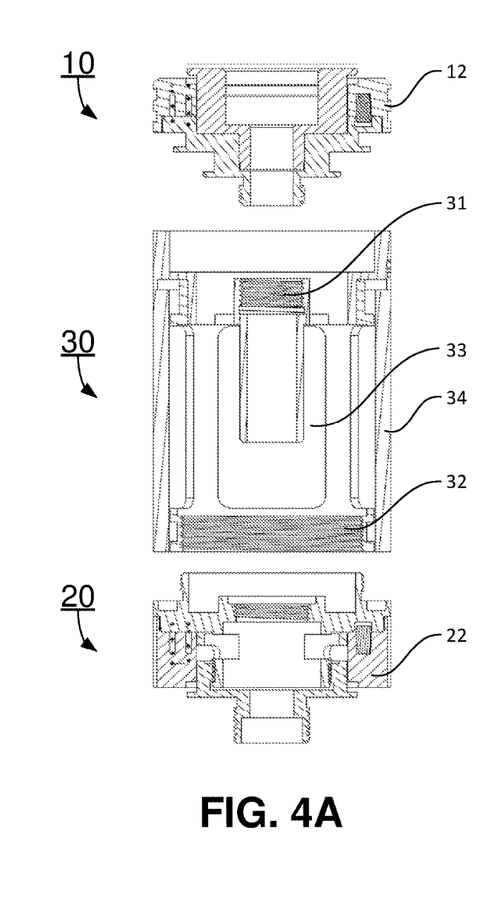
FIG. 4A is an exploded cross-sectional view of a part of the electronic cigarette having temper-proof locking mechanisms.

FIG. 4A shows an exploded cross-sectional view of a part of an electronic cigarette having temper-proof locking mechanisms in a locked position according to certain embodiments of the present invention.

Figure 4B:
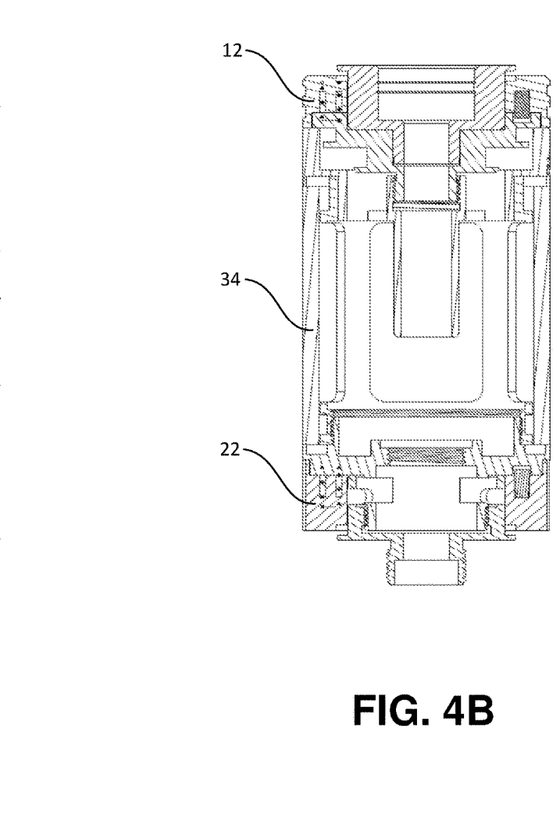
FIG. 4B is a cross-sectional view of the electronic cigarette having temper-proof locking mechanisms, both in a locked position according to certain embodiments of the present invention.

FIG. 4B shows a cross-sectional view of the assembled part of the electronic cigarette having temper-proof locking mechanisms in a locked position according to certain embodiments of the present invention. When the temper-proof mouthpiece connector locking mechanism 10 is in a locked position, there will not be any gap between the mouthpiece connector temper-proof ring 12 and the electronic cigarette body 30. When the temper-proof power connector locking mechanism 20 is in a locked position, there will not be any gap between the power connector temper-proof ring 22 and the electronic cigarette body 30.

Figure 5:
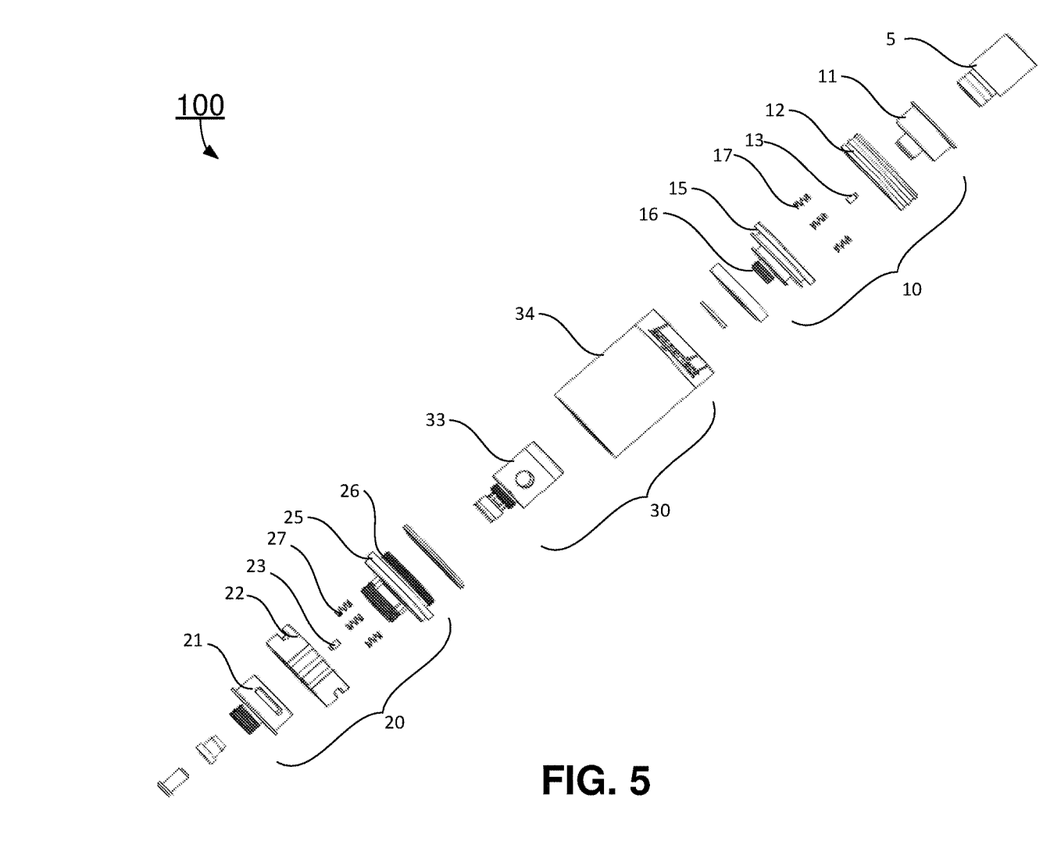
FIG. 5 is an exploded perspective view of an electronic cigarette having temper-proof locking mechanisms according to certain embodiments of the present invention.

In yet another aspect, the present invention relates to an electronic cigarette 100 having a temper-proof locking mechanisms. Referring now to FIG. 5, an exploded perspective view of the electronic cigarette 100 having temper-proof locking mechanisms is shown according to certain embodiments of the present invention.

In certain embodiments, the electronic cigarette 100 may include: an electronic cigarette body 30 having a mouthpiece connector inside thread 31 (not shown) and a power connector inside thread 32 (not shown), a temper-proof mouthpiece connector locking mechanism 10 threadedly connected to the mouthpiece connector inside thread 31 of the electronic cigarette body 30, and a temper-proof power connector locking mechanism 20 threadedly connected to the power connector inside thread 32 of the electronic cigarette body 30.

In certain embodiments, the electronic cigarette 100 may include an e-liquid storage tank (not shown) inside the electronic cigarette body 30, a vaporizer 33. The vaporizer 33 may include a heater (not shown in FIG. 5), and one or more e-liquid storage media (not shown).

In certain embodiments, the electronic cigarette 100 may also include: a mouthpiece 5 connected to the mouthpiece connector 11, and a power source connected to the power connector 21. The power source may include a positive terminal and a negative terminal, and an insulation layer between the positive terminal, and the negative terminal.

In certain embodiments, when a user pushes the temper-proof mouthpiece connector locking mechanism 10 towards the electronic cigarette body 30, the temper-proof mouthpiece connector locking mechanism 10 is locked such that the user is able to remove a mouthpiece connector from the electronic cigarette body 30 to refill e-liquid into the e-liquid storage tank for the electronic cigarette 100. When the user pushes the temper-proof power connector locking mechanism 20 towards the electronic cigarette body 30, the temper-proof power connector locking mechanism 20 is locked such that the user is able to remove a power connector from the electronic cigarette body 30 to replace a vaporizer, a heater for the vaporizer, and e-liquid storage medium of the electronic cigarette 100.

In certain embodiments, the temper-proof mouthpiece connector locking mechanism 10 may include: a mouthpiece connector base 15, a mouthpiece connector 11, a mouthpiece connector temper-proof ring 12, one or more mouthpiece connector locking pins 13, and one or more mouthpiece connector locking springs 17. The mouthpiece connector base 15 may include a mouthpiece connector outside thread 16 configured to threadedly connect to a mouthpiece connector inside thread 31 of an electronic cigarette body 30. The mouthpiece connector base 15 defines one or more mouthpiece connector locking openings 14. The mouthpiece connector 11 may be fixedly connected to the mouthpiece connector base 15. The mouthpiece connector temper-proof ring 12 may be positioned outside of the mouthpiece connector 11 for preventing mouthpiece connector tempering.

The temper-proof mouthpiece connector locking mechanism 10 may include an equal number of mouthpiece connector locking pins 13 as the one or more mouthpiece connector locking openings 14.

In certain embodiments, when a user pushes the mouthpiece connector temper-proof ring 12 towards the mouthpiece connector base 15 against a resilient force of the one or more mouthpiece connector locking springs 17, each of the one or more mouthpiece connector locking pins 13 engages a corresponding one of the one or more mouthpiece connector locking openings 14 such that the user can remove the mouthpiece connector 11 from the electronic cigarette body 30 by turning the temper-proof mouthpiece connector locking mechanism 10, and when the user releases the mouthpiece connector temper-proof ring 12, each of the one or more mouthpiece connector locking pins 13 disengages the corresponding one of the one or more mouthpiece connector locking openings 14 at the resilient force of the one or more mouthpiece connector locking springs 17 such that the user will not be able to remove the mouthpiece connector 11 from the electronic cigarette body 30.

In certain embodiments, the one or more mouthpiece connector locking pins 13 are substantially evenly distributed along a top surface of the mouthpiece connector base 15, and the corresponding one or more mouthpiece connector locking openings 14 are substantially evenly distributed along an inside edge of the mouthpiece connector 11, respectively, such that each of the one or more mouthpiece connector locking pins 13 engages a corresponding one of the one or more mouthpiece connector locking openings 14 when the user pushes the mouthpiece connector temper-proof ring 12 towards the mouthpiece connector base 15.

In one embodiment, the temper-proof mouthpiece connector locking mechanism 10 may include three mouthpiece connector locking springs 17 substantially evenly distributed along the top surface of the mouthpiece connector base 15.

In one embodiment, the temper-proof mouthpiece connector locking mechanism 10 may include one mouthpiece connector locking pin 13 and one corresponding mouthpiece connector locking opening 14. In another embodiment, the temper-proof mouthpiece connector locking mechanism 10 may include three mouthpiece connector locking pins 13 and three corresponding mouthpiece connector locking openings 14, respectively.

In certain embodiments, the temper-proof power connector locking mechanism 20 may include: a power connector base 25, a power connector 21, a power connector temper-proof ring 22, one or more power connector locking pins 23, and one or more power connector locking springs 27. The power connector base 25 may include a power connector outside thread 26 configured to threadedly connect to a power connector inside thread 32 of an electronic cigarette body 30. The power connector base 25 defines one or more power connector locking openings 24. The power connector 21 may be fixedly connected to the power connector base 25. The power connector temper-proof ring 22 may be positioned outside of the power connector 21 for preventing power connector tempering. The temper-proof power connector locking mechanism 20 may include an equal number of power connector locking pins 23 as the one or more power connector locking openings 24.

In certain embodiments, when a user pushes the power connector temper-proof ring 22 towards the power connector base 25 against a resilient force of the one or more power connector locking springs 27, each of the one or more power connector locking pins 23 engages a corresponding one of the one or more power connector locking openings 24 such that the user can remove the power connector 21 from the electronic cigarette body 30 by turning the temper-proof power connector locking mechanism 20.

In certain embodiments, when the user releases the power connector temper-proof ring 22, each of the one or more power connector locking pins 23 disengages the corresponding one of the one or more power connector locking openings 24 at the resilient force of the one or more power connector locking springs 27 such that the user will not be able to remove the power connector 21 from the electronic cigarette body 30.

In certain embodiments, when the power connector 21 is removed from the electronic cigarette body 30, the user may replace a vaporizer of the electronic cigarette, a heater for the vaporizer, and an e-liquid storage medium.

In certain embodiments, the one or more power connector locking pins 23 are substantially evenly distributed along a bottom surface of the power connector temper-proof ring 22, and the corresponding one or more power connector locking openings 24 are substantially evenly distributed along a top surface of the power connector base 25, respectively, such that each of the one or more power connector locking pins 23 engages a corresponding one of the one or more power connector locking openings 24 when the user pushes the power connector temper-proof ring 22 towards the power connector base 25.

In certain embodiments, the temper-proof power connector locking mechanism 20 may include three power connector locking springs 27 substantially evenly distributed along the bottom surface of the power connector temper-proof ring 22.

In one embodiment, the temper-proof power connector locking mechanism 20 may include one power connector locking pin 23 and one corresponding power connector locking opening 24. In another embodiment, the temper-proof power connector locking mechanism 20 may include three power connector locking pins 23 and three corresponding power connector locking opening 24, respectively.

In certain embodiments, each of the one or more mouthpiece connector locking pins 13 and each of the one or more power connector locking pins 23 may include: a round shape, a square shape, a triangular shape, a rectangular shape, an oval shape, and a combination of these shapes.

Figure 6A:
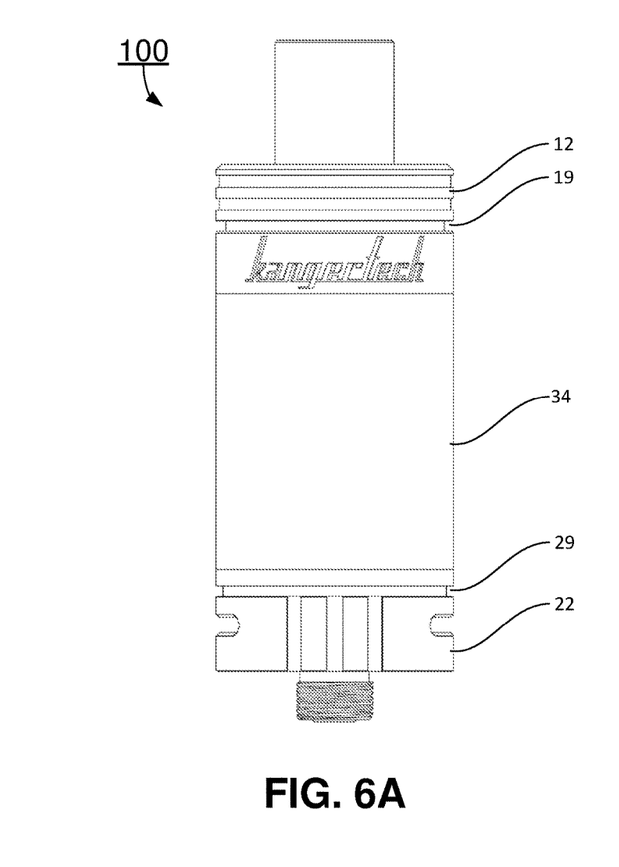
FIG. 6A is a side view of the electronic cigarette having temper-proof locking mechanisms.
Figure 6B:
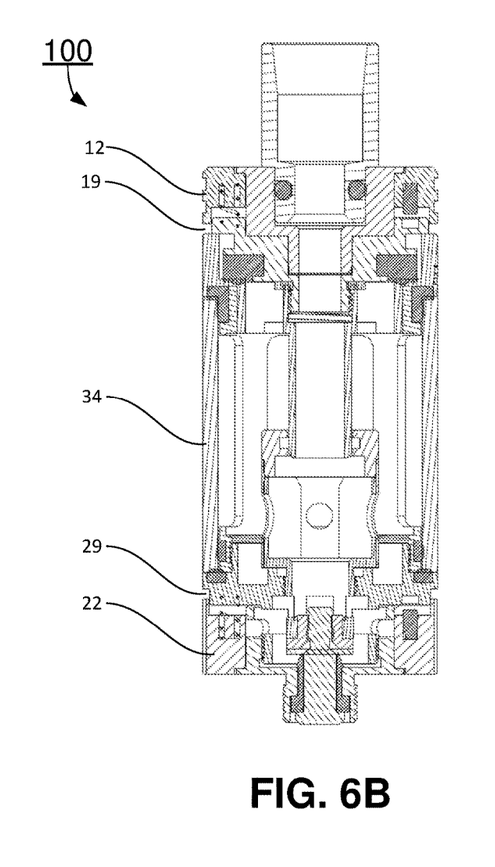
FIG. 6B is a cross-sectional view of the electronic cigarette having temper-proof locking mechanisms, both in an unlocked position, according to certain embodiments of the present invention.

FIG. 6A shows a side view of the electronic cigarette having temper-proof locking mechanisms, and FIG. 6B shows a cross-sectional view of the electronic cigarette having temper-proof locking mechanisms, both in an unlocked position, according to certain embodiments of the present invention. When the temper-proof mouthpiece connector locking mechanism 10 is in an unlocked position, a first gap 19 may appear between the mouthpiece connector temper-proof ring 12 and the electronic cigarette body 30. When the temper-proof power connector locking mechanism 20 is in an unlocked position, a second gap 29 may appear between the power connector temper-proof ring 22 and the electronic cigarette body 30.

Figure 7A:
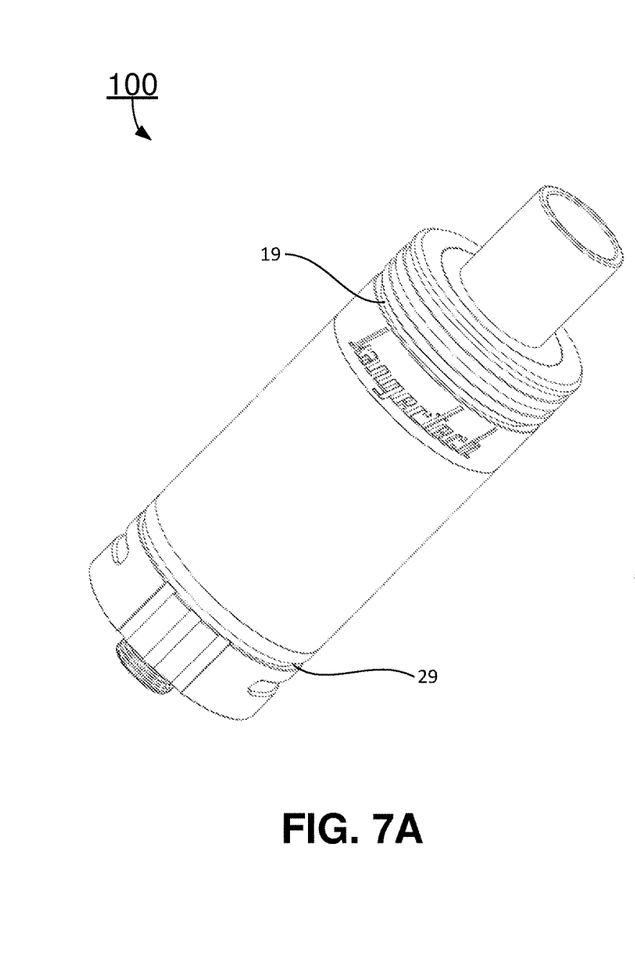
FIG. 7A is a perspective view of the electronic cigarette having temper-proof locking mechanisms in an unlocked position.

FIG. 7A shows a perspective view of the electronic cigarette having temper-proof locking mechanisms in an unlocked position. When the temper-proof mouthpiece connector locking mechanism 10 is in an unlocked position, a first gap 19 may appear between the mouthpiece connector temper-proof ring 12 and the electronic cigarette body 30. When the temper-proof power connector locking mechanism 20 is in an unlocked position, a second gap 29 may appear between the power connector temper-proof ring 22 and the electronic cigarette body 30.

Figure 7B:
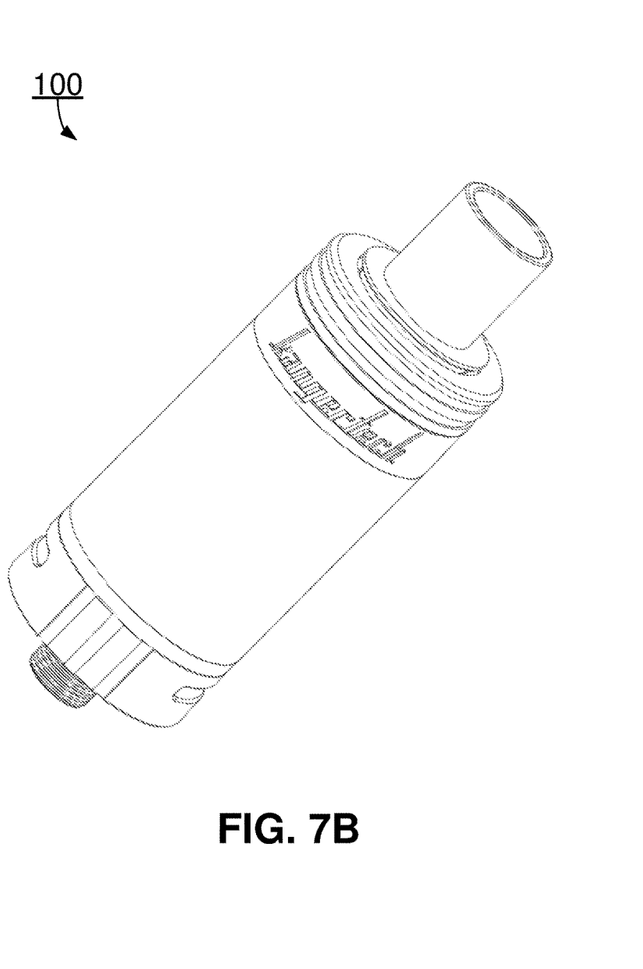
FIG. 7B is a perspective view of the electronic cigarette having temper-proof locking mechanisms in a locked position, according to certain embodiments of the present invention.

FIG. 7B is a perspective view of the electronic cigarette having temper-proof locking mechanisms in a locked position, according to certain embodiments of the present invention. When the temper-proof mouthpiece connector locking mechanism 10 is in a locked position, there will not be any gap between the mouthpiece connector temper-proof ring 12 and the electronic cigarette body 30. When the temper-proof power connector locking mechanism 20 is in a locked position, there will not be any gap between the power connector temper-proof ring 22 and the electronic cigarette body 30.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims, the foregoing description and the exemplary embodiments described therein, and accompanying drawings.

What is claimed is:

1. An electronic cigarette comprising:
    an electronic cigarette body having a mouthpiece connector inside thread and a power connector inside thread;
    a tamper-proof mouthpiece connector locking mechanism threadedly connected to the mouthpiece connector inside thread of the electronic cigarette body; and
    a tamper-proof power connector locking mechanism threadedly connected to the power connector inside thread of the electronic cigarette body,
    wherein when a user pushes the tamper-proof mouthpiece connector locking mechanism towards the electronic cigarette body, the tamper-proof mouthpiece connector locking mechanism is locked such that the user is able to remove a mouthpiece connector from the electronic cigarette body to refill e-liquid for the electronic cigarette, and when the user pushes the tamper-proof power connector locking mechanism towards the electronic cigarette body, the tamper-proof power connector locking mechanism is locked such that the user is able to remove a power connector from the electronic cigarette body to replace a vaporizer, a heater for the vaporizer, and e-liquid storage medium of the electronic cigarette.

2. The electronic cigarette of claim 1, wherein the tamper-proof mouthpiece connector locking mechanism comprises:
    a mouthpiece connector base having a mouthpiece connector outside thread configured to threadedly connect to the mouthpiece connector inside thread of the electronic cigarette body, wherein the mouthpiece connector base defines one or more mouthpiece connector locking openings;
    a mouthpiece connector fixedly connected to the mouthpiece connector base;
    a mouthpiece connector tamper-proof ring positioned outside of the mouthpiece connector configured to prevent mouthpiece connector tampering;
    one or more mouthpiece connector locking pins, one for each of the one or more mouthpiece connector locking openings; and
    one or more mouthpiece connector locking springs,
    wherein when a user pushes the mouthpiece connector tamper-proof ring towards the mouthpiece connector base against a resilient force of the one or more mouthpiece connector locking springs, each of the one or more mouthpiece connector locking pins engages a corresponding one of the one or more mouthpiece connector locking openings such that the user can remove the mouthpiece connector from the electronic cigarette body by turning the tamper-proof mouthpiece connector locking mechanism, and when the user releases the mouthpiece connector tamper-proof ring, each of the one or more mouthpiece connector locking pins disengages the corresponding one of the one or more mouthpiece connector locking openings at the resilient force of the one or more mouthpiece connector locking springs such that the user will not be able to remove the mouthpiece connector from the electronic cigarette body.

3. The electronic cigarette of claim 2, wherein the one or more mouthpiece connector locking pins are substantially evenly distributed along a top surface of the mouthpiece connector base, and the corresponding one or more mouthpiece connector locking openings are substantially evenly distributed along an inside edge of the mouthpiece connector, and wherein each of the one or more mouthpiece connector locking pins comprises: a round shape, a square shape, a triangular shape, a rectangular shape, an oval shape, and a combination thereof.

4. The electronic cigarette of claim 2, wherein the tamper-proof mouthpiece connector locking mechanism comprises three mouthpiece connector locking springs substantially evenly distributed along the top surface of the mouthpiece connector tamper-proof ring.

5. The electronic cigarette of claim 1, wherein the tamper-proof power connector locking mechanism comprising:
    a power connector base having a power connector outside thread configured to threadedly connect to the power connector inside thread 31 of the electronic cigarette body, wherein the power connector base defines one or more power connector locking openings;
    a power connector fixedly connected to the power connector base;
    a power connector tamper-proof ring positioned outside of the power connector configured to prevent power connector tampering;
    one or more power connector locking pins, one for each of the one or more power connector locking openings; and
    one or more power connector locking springs,
    wherein when a user pushes the power connector tamper-proof ring towards the power connector base against a resilient force of the one or more power connector locking springs, each of the one or more power connector locking pins engages a corresponding one of the one or more power connector locking openings such that the user can remove the power connector from the electronic cigarette body by turning the tamper-proof power connector locking mechanism, and when the user releases the power connector tamper-proof ring, each of the one or more power connector locking pins disengages the corresponding one of the one or more power connector locking openings at the resilient force of the one or more power connector locking springs such that the user will not be able to remove the power connector from the electronic cigarette body.

6. The electronic cigarette of claim 5, wherein the one or more power connector locking pins are substantially evenly distributed along a bottom surface of the power connector tamper-proof ring, and the corresponding one or more power connector locking openings are substantially evenly distributed along a top surface of the power connector base, and wherein each of the one or more power connector locking pins comprises: a round shape, a square shape, a triangular shape, a rectangular shape, an oval shape, and a combination thereof.

7. The electronic cigarette of claim 5, wherein the tamper-proof power connector locking mechanism comprises three power connector locking springs substantially evenly distributed along the bottom surface of the bottom surface of the power connector tamper-proof ring.

8. The electronic cigarette of claim 1, wherein the electronic cigarette further comprises:
  a mouthpiece connected to the mouthpiece connector; and
  a power source connected to the power connector, wherein the power source comprises a positive terminal and a negative terminal, and an insulation layer between the positive terminal, and the negative terminal.

* * * * *